United States Patent [19]
Ferry et al.

[11] Patent Number: 6,147,095
[45] Date of Patent: *Nov. 14, 2000

[54] METHOD FOR IMPROVING THE PHARMACOKINETICS OF TIPRANAVIR

[75] Inventors: James J. Ferry, Kalamazoo; John R. Baldwin, Portage; Marie T. Borin, Kalamazoo, all of Mich.

[73] Assignee: Pharmacia & Upjohn Company, Kalamazoo, Mich.

[*] Notice: This patent issued on a continued prosecution application filed under 37 CFR 1.53(d), and is subject to the twenty year patent term provisions of 35 U.S.C. 154(a)(2).

[21] Appl. No.: 09/430,742

[22] Filed: Oct. 29, 1999

Related U.S. Application Data
[60] Provisional application No. 60/106,963, Nov. 4, 1998.

[51] Int. Cl.[7] ................................................ A61K 31/44
[52] U.S. Cl. .......................................................... 514/336
[58] Field of Search ............................................ 514/336

[56] References Cited

U.S. PATENT DOCUMENTS

| | | | |
|---|---|---|---|
| 5,843,990 | 12/1998 | Baker | 514/455 |
| 5,932,570 | 8/1999 | Rodgers et al. | 514/218 |

FOREIGN PATENT DOCUMENTS

| | | | |
|---|---|---|---|
| WO 97/01349 | 1/1997 | WIPO | A61K 38/06 |
| WO 98/22106 | 5/1998 | WIPO | A61K 31/425 |

OTHER PUBLICATIONS

A Cato III, J Cavanaugh, H Shi, A Hsu, J Leonard, R Granneman,"The effect of multiple doses of ritonavir on the pharmacokinetics of rifabutin, " Clinical Pharmacology & Therapeutics, Apr. 1998, vol. 63, No. 4:414–421.

A Cato III, J Qian, A Hsu, B Levy, J Leonard, R Granneman, "Multidose Pharmacokinetics of Ritonavir and Zidovudine in Human Immunodeficiency Virus–Infected Patients," Antimicrobial Agents an Chemotherapy, Jul. 1998, vol. 42:1788–1793.

VK Chaudhary, T Mizukami, TR Fuerst, DJ FitzGerald, B Moss, I Pastan, EA Berger, "Selective killing of HIV–infected cells by recombinant human CD4–Pseudomonas exotoxin hybrid protein," Nature, 1988, 335:369–372.

KT Chong, PJ Pagano, "In Vitro Combination of PNU–140690, A Human Immunodeficiency Virus Type 1 Protease Inhibitor, with Ritonavir against Ritonavir–Sensitive and –Resistant Clinical Isolates," Antimicrobial Agents and Chemotherapy, Nov. 1997, vol. 41, No. 11:2367–2373.

PL Darke, C–T Leu, LJ Davis, JC Heimbach, RE Diehl, WS Hill, RAF Dixon, IS Sigal,"Human Immunodeficiency Virus Protease," J. Biol. Chem., 1989, 264:2307–2312.

PL Darke, RF Nutt, SF Brady, VM Garsky, TM Ciccarone, C–T Leu, PK Lumma, RM Freidinger, DF Veber, IS Sigal, "HIV–1 Protease Specificity of Peptide Cleavage is Sufficient," Biochem. Biophys. Res. Communs., 1988, 156:297–303.

KC Deen, JS McDougal, R Inacker, G Folena–Wasserman, J Arthos, J Rosenberg, PJ Maddon, R Axel, RW Sweet, "A Soluble form of CD4 (T4) protein inhibits AIDS virus infection," Nature, 1998, 331:82–84.

P Duesberg, "Human Immunodeficiency virus and acquired immunodeficiency syndrome: Correlation but not causation," Proc. Natl. Acad. Sci., USA, 1989 86:755–764.

RA Fisher, JM Bertonis, W Meier, VA Johnson, DS Costopoulos, T Liu, R Tizard, BD Walker, MS Hirsch, RT Schooley, RA Flavell, "HIV infection is Blocked in vitro by recombinant soluble CD4," Nature, 1988, 331:76–78.

C–Z Giam, I Borsos, "In Vivo and in Vitro Autoprocessing of Human Immunodeficiency Virus Protease Expressed in Escherichia coli," J. Biol. Chem., 1988, 263:14617–14620.

J Hansen, S Billich, T Schulze, S Sukrow, K Moelling, "Partial purification and substrate analysis of bacterially expressed HIV protease by means of monoclonal antibody," EMBO J., 1988 7:1785–1791.

A Hsu, GR Granneman, G Cao, L Carothers, R El–Shourbagy, P Baroldi, K Erdman, F Brown, E Sun, JM Leonard, "Pharmacokinetic interactions between two human immunodeficiency virus protease inhibitors, ritonavir and saquinavir," Clinical Pharmacology & Therapeutics, Apr. 1998, vol. 63, No.4:453–464.

RE Hussey, NE Richardson, M Kowalski, NR Brown, H–C Chang, RF Siliciano, T Dorfman, B Walker, J Sodroski, EL Reinherz, "A Soluble CD4 protein selectively inhibits HIV replication and syncytium formation," Nature, 1988, 331:78–81.

I Katoh, T Yasunaga, Y Ikawa, Y Yoshinaka, "Inhibition of retroviral protease activity by an aspartyl proteinase inhibitor," Nature, 1987 329:654–656.

NE Kohl, EA Emini, WA Schleif, LJ Davis JC Heimbach, RAF Dixon, EM Scolnick, IS Sigal, "Active human immunodeficiency virus protease is required for viral infectivity," Proc. Natl. Acad. Sci., USA, 1988 85:4686–4690.

JA Martin, "Recent advances in the design of HIV proteinase inhibitors," Antiviral Research, 1992, 17:265–278.

TJ McQuade, AG Tomasselli, L Liu, V Karacostas, B Moss, TK Sawyer, RL Heinrikson, WG Tarpley, "A Synthetic HIV–1 Protease Inhibitor with Antiviral Activity Arrests HIV–Like Particle Maturation," Science, 1990, 247:454–456.

M Miller, M Jaskolski, JK Mohana Rao, J Leis, A Wlodawer, "Crystal structure of a retroviral protease proves relationship to aspartic protease family," Nature, 1989, 337:576–579.

(List continued on next page.)

Primary Examiner—Raymond Henley, III
Attorney, Agent, or Firm—Lucy X. Yang

[57] ABSTRACT

The present invention relates to a novel method for improving the pharmacokinetics of tipranavir, comprising administering to a human in need of such treatment a combination of a therapeutically effective amount of tipranavir or a pharmaceutically acceptable salt thereof, and a therapeutically effective amount of ritonavir or a pharmaceutically acceptable salt thereof.

14 Claims, 7 Drawing Sheets

OTHER PUBLICATIONS

MA Muesing, DH Smith, CD Cabradilla, CV Benton, LA Lasky, DJ Capon, "Nucleic acid structure and expression of the human AIDS/lymphadenopathy retrovirus," Nature, 1985, 313:450–458.

MA Navia, PMD Fitzgerald, BM McKeever, C–T Leu, JC Heimbach, WK Herber, IS Sigal, PL Darke, JP Springer, "Three–dimensional structure of aspartyl protease from human immunodeficiency virus HIV–1," Nature, 1989, 337:615–620.

RF Nutt, SF Brady, PL Darke, TM Ciccarone, CD Colton, EM Nutt, JA Rodkey, CD Bennett, LH Waxman, Is. Sigal, PS Anderson, Df Veber, "Chemical synthesis and enzymatic activity opf a 99–residue peptide with a sequence proposed for the human immunodeficiency virus protease," Proc. Natl. Acad. Sci., USA, 1988, 85:7129–7133.

D Ouellet, A Hsu, J Qian, CS Locke, CJ Eason, JH Cavanaugh, JM Leonard, GR Granneman, "Effect of ritonavir on the pharmacokinetics of ethinyl estradiol in heathy female volunteers," J. Clin Pharmacology, 1998, 46:111–116.

LH Pearl, WR Taylor, "A structural model for the retroviral proteases," Nature, 1987, 329:351–354.

L Ratner, W Haseltine, R Patarca, KJ Livak, B Starcich, SF Josephs, ER Doran, JA Rafalski, EA Whitehorn, K Baumeister, L Ivanoff, SR Petteway Jr., ML Pearson, JA Lautenberger, TS Papas, J Ghrayeb, NT Chang, RC Gallo, F Wong–Staal, "Complete nucleotide sequence of the AIDS virus, HTLV–III," Nature, 1985, 313:277–284.

R Sanchez–Pescador, MD Power, PJ Barr, KS Steimer, MM Stempein, SL Brown–Shimer, WW Gee, A Renard, A Randolph, JA Levy, D Dina, PA Luciw, "Nucleotide Sequence and Expression of an AIDS–Associated Retrovirus (ARV–2)," Science, 1985, 227:484–492.

J Schneider, SB Kent, SBH Kent, "Enzymatic Activity of a Synthetic 99 Residue Protein Corresponding to the Putative HIV–1 Protease," Cell, 1988, 54:363–368.

S Seelmeier, H Schmidt, V Turk, K von der Helm, "Human Immunodeficiency virus has an aspartic–type protease that can be inhibited by pepstatin A," Proc. Natl. Acad. Sci., USA, 1988, 85:6612–6616.

DH Smith, RA Byrn, SA Marsters, T Gregory, JE Groopman, DJ Capon, "Blocking of HIV–1 Infectivity by a Soluble, Secreted Form of the CD4 Antigen," Science, 1987, 238:1704–1707.

MA Till, V Ghetie, T Gregory, EJ Patzer, JP Porter, JW Uhr, DJ Capon, ES Vitetta, "HIV–Infected Cells Are Killed by rCD4–Ricin A Chain," Science, 1988, 242:1166–1168.

K von der Helm,"Cleavage of Rous sacorma viral polypeptide precursor into internal structural proteins in vitro involves viral protein p15," Proc. Natl. Acad. Sci., USA, 1977, 74:911–915.

S Wain–Hobson, P Sonigo, O Danos, S Cole, M Alizon, "Nucleotide Sequence of the AIDS Virus, LAV," Cell, 1985, 40:9–17.

Y Yoshinaka, I Katoh, TD Copeland, GW Smythers, S Oroszlan, "Bovine Leukemia Virus Protease: Purification, Chemical Analysis, and In Vitro Processing of gag Precursor Polyproteins," J. Virol., 1986, 57:826–832.

Y Yoshinaka, I Katoh, TD Copeland, S Oroszlan "Murine leukemia virus protease is encoded by the gag–pol gene and is synthesized through suppression of an amber termination codon," Proc. Natl. Acad. Sci., USA, 1985, 82:1618–1622.

Y Yoshinaka, I Katoh, TD Copeland, S Oroszlan "Translational Readthrough of an Amber Termination Codon During Synthesis of Feline Leukemia Virus Protease," J. Virol., 1985, 55:870–873.

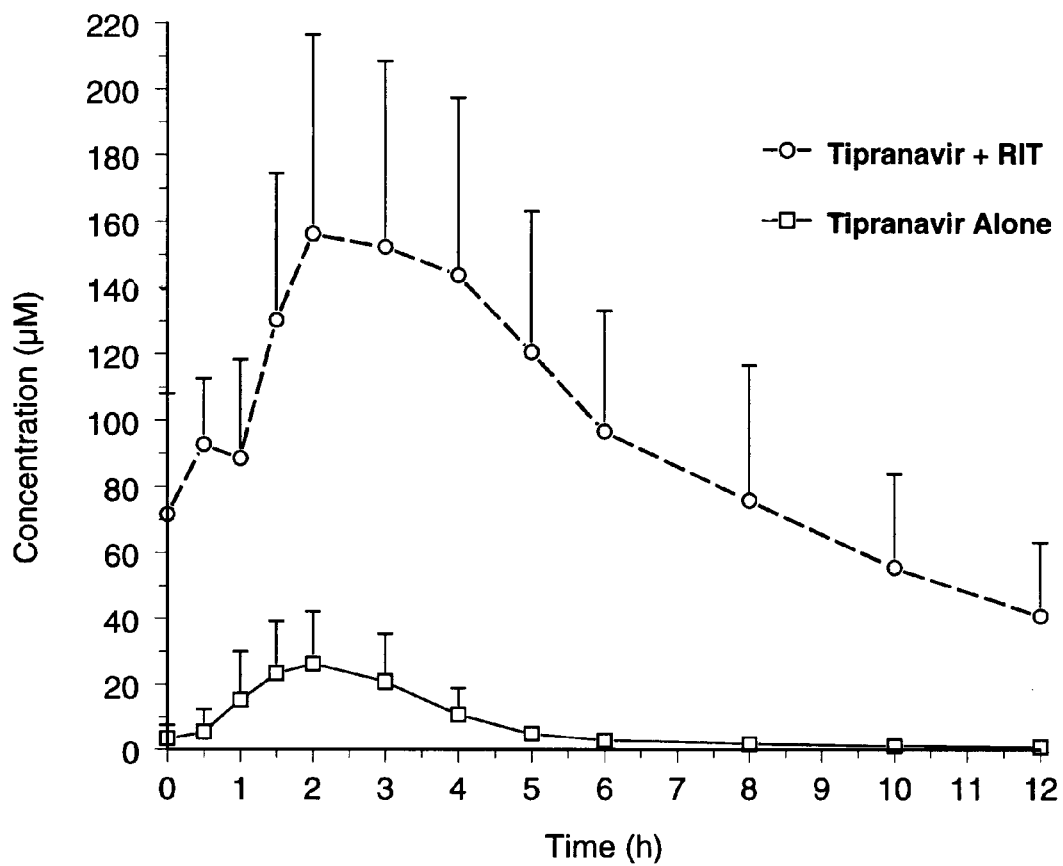
Figure 1. Mean (±SD) Plasma Tipranavir Concentrations (1350 mg BID Tipranavir / 500 mg BID RIT)

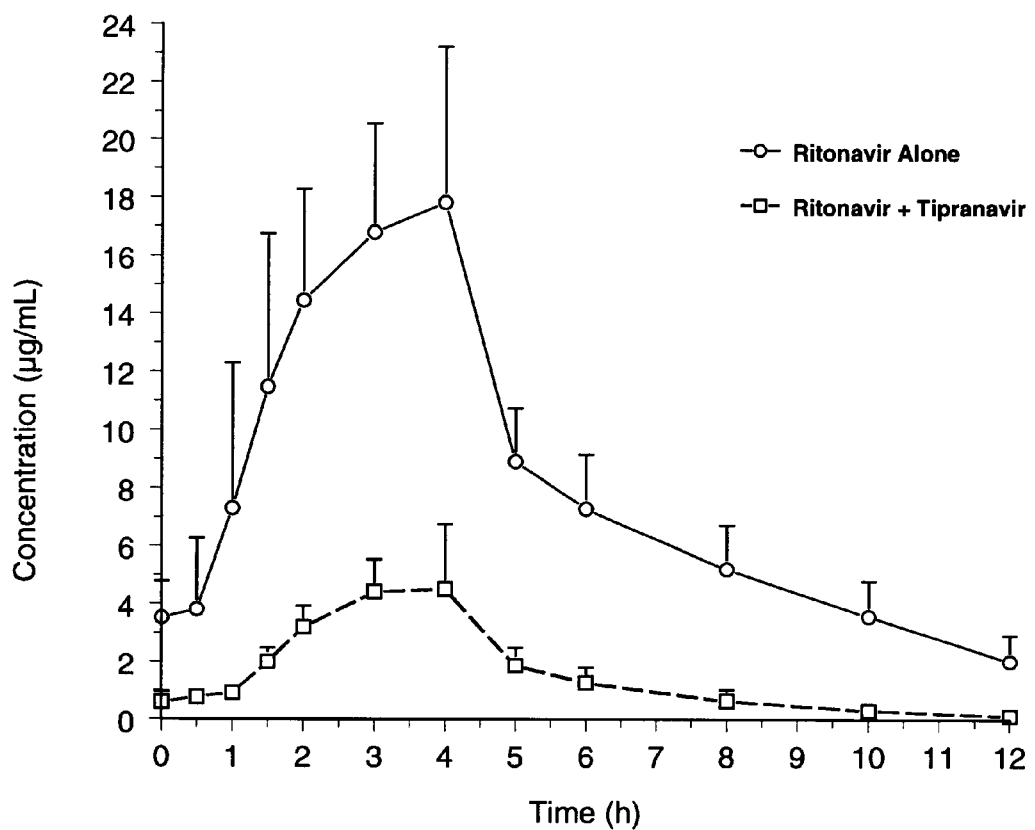
Figure 2. Mean (±SD) Plasma Ritonavir Concentrations (500 mg BID RIT / 1350 mg BID Tipranavir)

Figure 3. Mean (±SD) Plasma Ritonavir Concentrations after Ritonavir 500 mg BID Co-administered with Tipranavir 600 mg BID or Tipranavir 900 mg BID
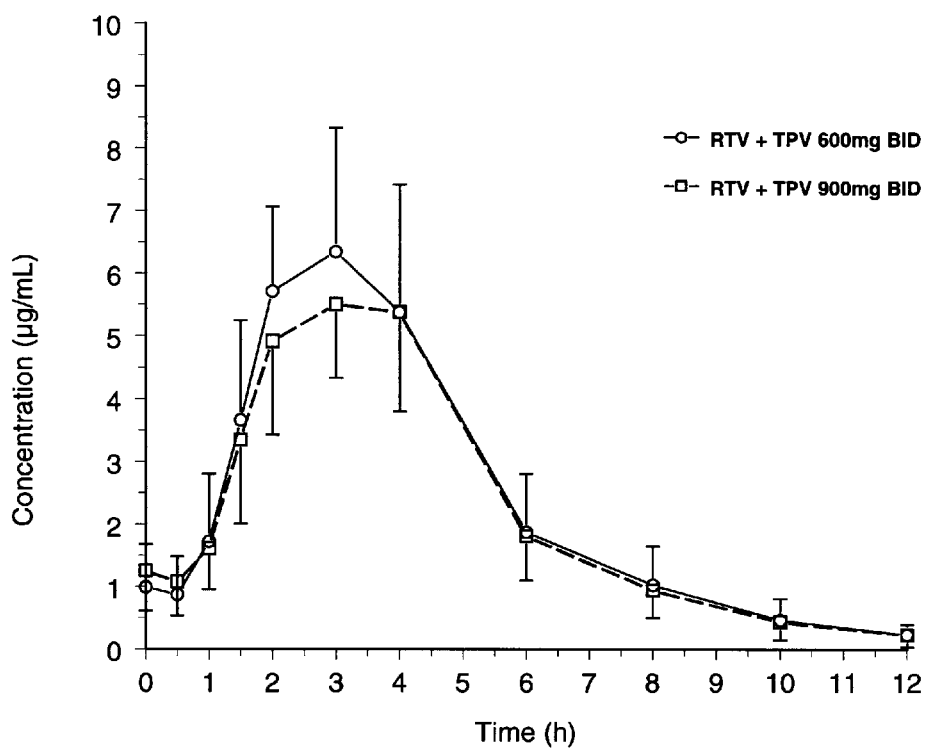

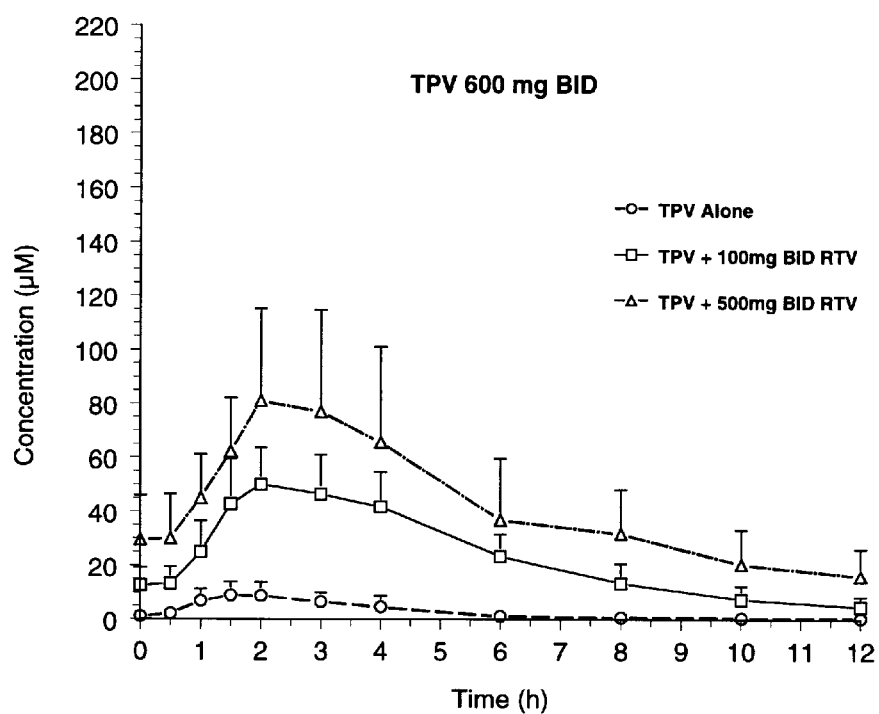
Figure 4. Mean (±SD) Plasma Tipranavir Concentrations after Tipranavir 600 mg BID Administered Alone, Concomitantly with Ritonavir 100 mg BID, or Concomitantly with Ritonavir 500 mg BID

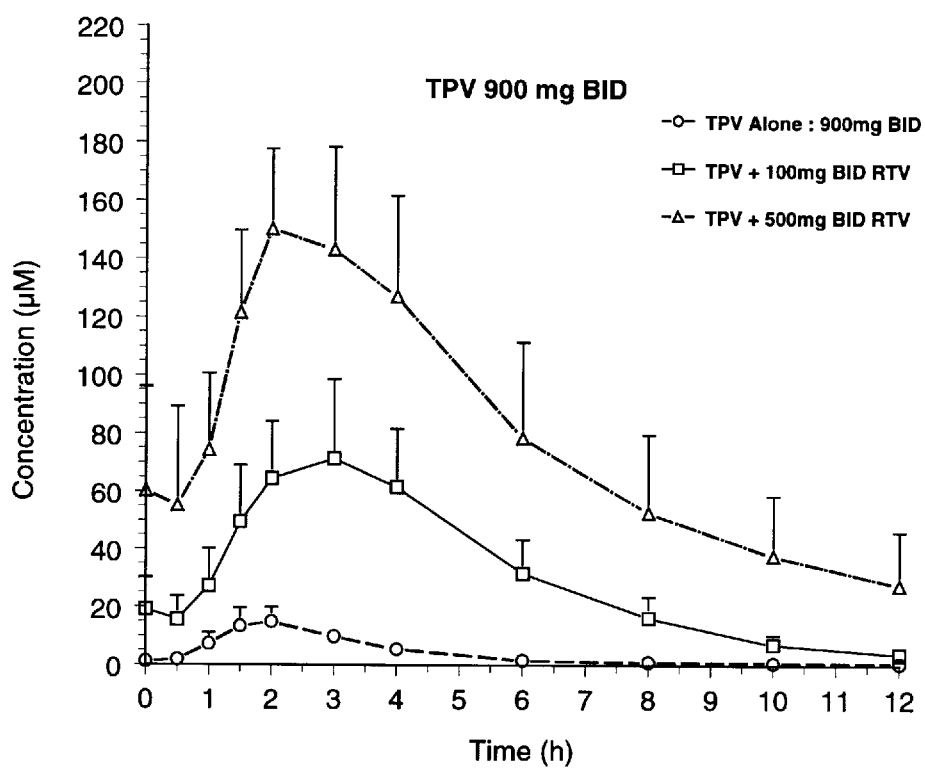
Figure 5. Mean (±SD) Plasma Tipranavir Concentrations after Tipranavir 900 mg BID Administered Alone, Concomitantly with Ritonavir 100 mg BID, or Concomitantly with Ritonavir 500 mg BID

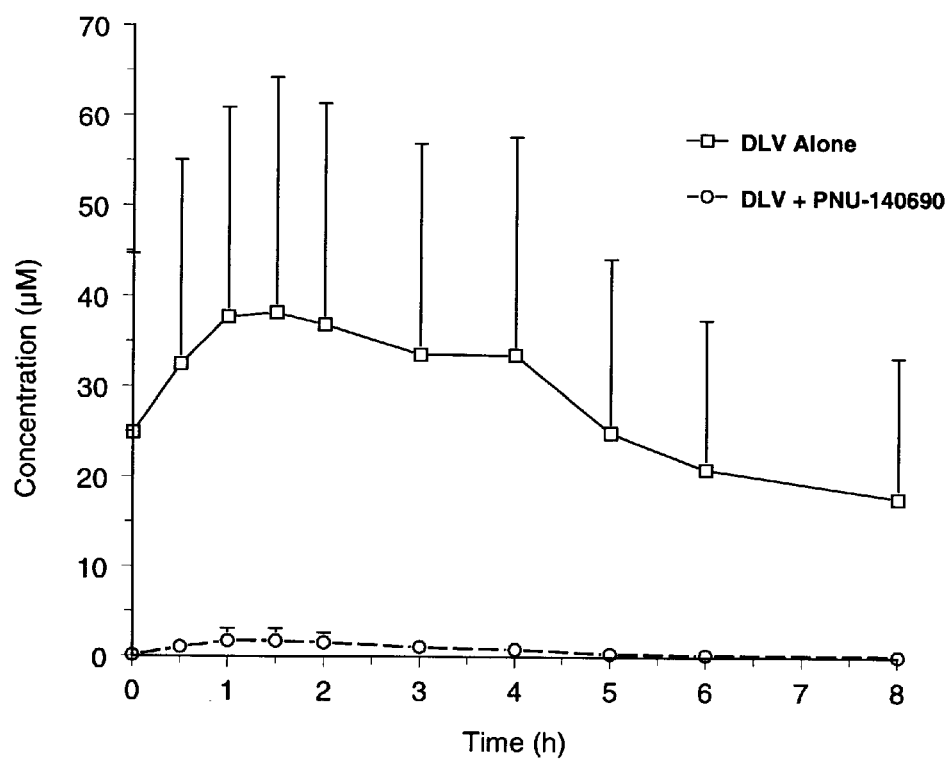
Figure 6. Mean (±SD) Plasma Delavirdine Concentrations (400 mg TID DLV / 1200 mg BID Tipranavir)

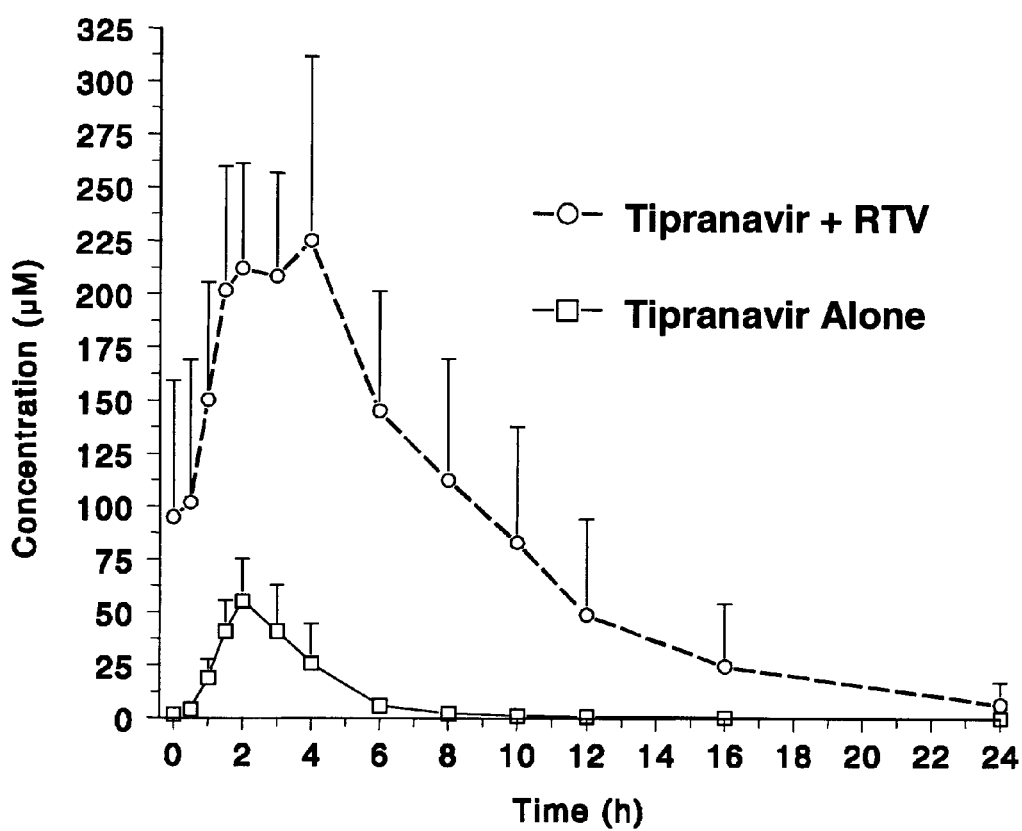
Figure 7. Mean (+SD) Plasma Tipranavir Concentrations (1250 mg BID Tipranavir / 200 mg BID Ritonavir)

METHOD FOR IMPROVING THE PHARMACOKINETICS OF TIPRANAVIR

CROSS-REFERENCE TO RELATED APPLICATIONS

This application claims the benefit of the following provisional application: U.S. Ser. No. 60/106,963, filed Nov. 4, 1998, under 35 USC §119(e)(1).

FIELD OF THE INVENTION

The present invention relates to a novel method for improving the pharmacokinetics of tipranavir, comprising administering to a human in need of such treatment a combination of a therapeutically effective amount of tipranavir or a pharmaceutically acceptable salt thereof, and a therapeutically effective amount of ritonavir or a pharmaceutically acceptable salt thereof.

BACKGROUND OF THE INVENTION

Since the first description of the malady in the early part of this decade, acquired immunodeficiency disease syndrome (AIDS) and its devastating consequences have been subjects of continuous and intense coverage in both the lay and scientific press. The literature on the disease and the virus is already so vast as to defy thorough citation.

Human immunodeficiency virus (HIV) has long been recognized as the causative agent in AIDS, although a minority opinion to the contrary has been expressed (e.g., P. Duesberg, Proc. Natl. Acad. Sci., USA, 86:755–764 (1989)). Sequence analysis of the complete genomes from several infective and non-infective HIV-isolates has shed considerable light on the make-up of the virus and the types of molecules that are essential for its replication and maturation to an infective species. The HIV protease is essential for the processing of the viral gag and gag-pol polypeptides into mature virion proteins. L. Ratner, et al., Nature, 313:277–284 (1985); L. H. Pearl and W. R. Taylor, Nature, 329:351 (1987). HIV exhibits the same gag/pol/env organization seen in other retroviruses. L. Ratner, et al., above; S. Wain-Hobson, et al., Cell, 40:9–17 (1985); R. Sanchez-Pescador, et al., Science, 227:484–492 (1985); and M. A. Muesing, et al., Nature, 313:450–458 (1985).

Reverse transcriptase (RT) is an enzyme unique to retroviruses that catalyzes the conversion of viral RNA into double stranded DNA. Blockage at any point during the transcription process by an aberrant deoxynucleoside triphosphate incapable of elongation, such as AZT (zidovudine), should have dramatic consequences relative to viral replication. Much work on the RT target is in progress based, in large measure, upon the fact that nucleosides like AZT are easily delivered to cells. However, the inefficiency of phosphorylation steps to the triphosphate, and the lack of specificity and consequent toxicity, constitute major drawbacks to use of AZT and similar nucleosides having a blocked, or missing, 3hydroxyl group.

The T4 cell receptor for HIV, the so-called CD4 molecule, has also been targeted as an intervention point in AIDS therapy. R. A. Fisher, et al., Nature, 331:76–78 (1988); R. E. Hussey, et al., Nature, 331:78–81 (1988); and K. C. Deen, et al., Nature, 331:82–84 (1988). The exterior portion of this transmembrane protein, a molecule of 371 amino acids (sCD4) has been expressed in Chinese hamster ovary (CHO) cells and Genentech (D. H. Smith, et al., Science, 238:1704–1707 (1987)) has had a product in clinical trials since the fall of 1987. CD4 has been shown to have a narrow spectrum of activity against wild-type virus and so far has failed to control HIV infection in humans. Schinazi, Mead and Feorino, page 963. The idea behind CD4 based therapy is that the molecules can neutralize HIV by interfering with viral attachment to T4, and other cells which express CD4 on their surfaces. A variant on this theme is to attach cell toxins to CD4 for specific binding and delivery to infected cells which display glycoprotein gp-120 on their surfaces. M. A. Till, et al., Science, 242:1166–1168 (1988); and V. K. Chaudhary, et al., Nature, 335:369–372 (1988).

Another therapeutic target in AIDS involves inhibition of the viral protease (or proteinase) that is essential for processing HIV-fusion polypeptide precursors. In HIV and several other retroviruses, the proteolytic maturation of the gag and gag/pol fusion polypeptides (a process indispensable for generation of infective viral particles) has been shown to be mediated by a protease that is, itself, encoded by the pol region of the viral genome. Y. Yoshinaka, et al., Proc. Natl. Acad. Sci. USA, 82:1618–1622 (1985); Y. Yoshinaka, et al., J. Virol., 55:870–873 (1985); Y. Yoshinaka, et al., J. Virol., 57:826–832 (1986); and K. von der Helm, Proc. Natl. Acad. Sci., USA, 74:911–915 (1977). Inhibition of the protease has been shown to inhibit the processing of the HIV p55 in mammalian cell and HIV replication in T lymphocytes. T. J. McQuade, et al., Science, 247:454 (1990).

The protease (or proteinase), consisting of only 99 amino acids, is among the smallest enzymes known, and its demonstrated homology to aspartyl proteases such as pepsin and renin (L. H. Pearl and W. R. Taylor, Nature, 329:351–354 (1987); and I. Katoh, et al., Nature, 329:654–656 (1987)), led to inferences regarding the three-dimensional structure and mechanism of the enzyme (L. H. Pearl and W. R. Taylor, above) that have since been borne out experimentally. Active HIV protease has been expressed in bacteria (see, e.g., P. L. Darke, et al., J. Biol. Chem., 264:2307–2312 (1989)) and chemically synthesized (J. Schneider and S. B. Kent, Cell, 54:363–368 (1988); and R. F. Nutt, et al., Proc. Natl. Acad. Sci., USA, 85:7129–7133 (1988)). Site directed mutagenesis (P. L. Darke, et al., above); and N. E. Kohl, et al., Proc. Nati. Acad. Sci., USA, 85:4686–4690 (1988)) and pepstatin inhibition (P. L. Darke, et al., J. Biol. Chem., 264:2307–2312 (1989); S. Seelmeier, et al., Proc. Natl. Acad. Sci., USA, 85:6612–6616 (1988); C.-Z. Giam and I. Borsos, J. Biol. Chem., 263:14617–14720 (1988); and J. Hansen, et al., EMBO J., 7:1785–1791 (1988)) have provided evidence for HIV protease's mechanistic function as an aspartyl protease. A study has demonstrated that the protease cleaves at the sites expected in peptides modeled after the regions actually cleaved by the enzyme in the gag and pol precursor proteins during viral maturation. P. L. Darke, et al., Biochem. Biophys. Res. Communs., 156:297–303 (1988). X-ray crystallographic analysis of the HIV-protease (M. A. Navia, et al., Nature, 337:615–620 (1989)) and a related retroviral enzyme from Rous sarcoma virus (M. Miller, et al., Nature, 337:576–579 (1989)) reveal an active site in the protcase dimer that is identical to that seen in other aspartyl proteases, thus supporting the supposition (L. H. Pearl and W. R. Taylor, above) that the HIV enzyme is active as a dimer. See also Joseph A. Martin, "Recent Advances in the Design of HIV Proteinase Inhibitors," Antiviral Research, 17 (1992) 265–278.

Current therapies for HIV infection focus on inhibiting the activity of the above-mentioned viral enzymes which are essential to the life cycle of the virus. The antiretrovirals that are presently in use may be divided into three classes, designated Nucleoside Reverse Transcriptase Inhibitors (NRTIs), Non-nucleoside Reverse Transcriptase Inhibitors (NNRTIs), and Protease Inhibitors (PIs). Presently, combination therapies, i.e. the selection of two or more antiretroviral agents taken together to make up a "drug cocktail," are the preferred treatment for HIV infection. Combination therapies have been shown to reduce the incidence of opportunistic infections and to increase survival time. Typically, the drug cocktail combines drugs from different classes, so as to attack the virus at several stages in the replication process. This approach has been shown to reduce the likelihood of the development of virus forms that are resistant to a given drug or class of drugs.

Typically, a drug cocktail will include two selections from the NRTIs, and one or more selections from the PI class. The choice of which drugs to combine must take into account synergistic effects of certain drug combinations, as well as other sorts of drug-drug interactions that might render a combination less effective or even dangerous.

One of the issues that must be considered when developing a combination therapy is the likelihood of patient compliance with the prescribed regimen. The use of several drugs, each having certain restrictions regarding how often and when it must be taken (before or after meals, or with certain types of food), frequently results in a complicated medication schedule and requires that a large number of pills be taken. Furthermore, each of the drugs is associated with a variety of side effects, which are generally related to the dosage level.

Thus, the search for a fully effective and safe means of inhibiting HIV infection while simplifying treatment regimens and reducing the side effects experienced by the patient, and thereby effectively treating diseases caused by such a virus, such as acquired immunodeficiency syndrome (AIDS), continues.

REFERENCES

WO 97/01349

WO 98/22106

Chong, K.-T., and P. J. Pagano, "In vitro Combination of PNU-140690, a Human Immunodeficiency Virus Type 1 Protease Inhibitor, with Ritonavir against Ritonavir Sensitive and -Resistant Clinical Isolates," *Antimicrobial Agents and Chemotherapy* 41(11): 2367–2374 (November 1997).

SUMMARY OF THE INVENTION

The present invention provides a method for improving the pharmacokinetics of tipranavir, comprising administering to a human in need of such treatment a combination of a therapeutically effective amount of tipranavir or a pharmaceutically acceptable salt thereof, and a therapeutically effective amount of ritonavir or a pharmaceutically acceptable salt thereof. Also, the present invention provides a method for increasing human blood levels of tipranavir, comprising administering to a human in need of such treatment a combination of a therapeutically effective amount of tipranavir or a pharmaceutically acceptable salt thereof, and a therapeutically effective amount of ritonavir or a pharmaceutically acceptable salt thereof.

BRIEF DESCRIPTION OF THE FIGURES

FIG. 1: FIG. 1 is a graph showing mean (±SD) plasma tipranavir concentrations (1350 mg BID tipranavir/500 mg BID ritonavir).

FIG. 2: FIG. 2 is a graph showing mean (±SD) plasma ritonavir concentrations (1350 mg BID tipranavir/500 mg BID ritonavir).

FIG. 3: FIG. 3 is a graph showing mean (±SD) plasma ritonavir concentrations after 500 mg BID ritonavir co-administered with 600 mg BID tipranavir or 900 mg BID tipranavir.

FIG. 4: FIG. 4 is a graph showing mean (±SD) plasma tipranavir concentrations after 600 mg BID tipranavir administered alone, concomitantly with ritonavir 100 mg BID, or concomitantly with 500 mg BID ritonavir.

FIG. 5: FIG. 5 is a graph showing mean (±SD) plasma tipranavir concentrations after tipranavir 900 mg BID administered alone, concomitantly with ritonavir 100 mg BID, or concomitantly with 500 mg BID ritonavir.

FIG. 6: FIG. 6 is a graph showing mean (±SD) plasma delavirdine concentrations (400 mg TID DLV/1200 mg BID tipranavir).

FIG. 7: FIG. 7 is a graph showing Mean (+SD) Plasma Tipranavir Concentrations (1250 mg BID Tipranavir/200 mg BID Ritonavir)

DETAILED DESCRIPTION

Definitions: The following symbols and abbreviations of standard pharmacokinetic terminology are used throughout the Detailed Description and the Examples, below.

| | |
|---|---|
| $\lambda z$ | Apparent terminal elimination rate constant |
| $\tau$ | Dosing interval |
| At | Amount of drug absorbed to time t |
| Ae | Amount of drug excreted in urine |
| AUC0-t | Area under the concentration-time curve from time zero to time t |
| AUC0-t(last) | Area under the concentration-time curve from time zero to last detectable serum concentration |
| AUC0-$\tau$ | Area under the concentration-time curve within a dosing interval |
| AUC0-$\infty$ | Area under the concentration-time curve from time zero to infinity |
| AUCIV | Area under the concentration-time curve after IV drug administration |
| AUCPO | Area under the concentration-time curve after oral drug adminnistration |
| AUCPO(0–24) | Area under the concentration-time curve indicating route and time interval |
| AUMC0-t | Area under the moment curve from time zero to time t |
| AUMC0-t(last) | Area under the moment curve from time zero to last detectable serum concentration |
| AUMC0-$\infty$ | Area under the moment curve from time zero to infinity |
| C0 | Concentration of drug at time zero |
| CL | Systemic clearance |
| CLPO | Oral clearance |
| CLNR | Non-renal clearance |
| CLR | Renal clearance |
| Cmax | Maximum serum/plasma drug concentration |
| Cmin | Minimum serum/plasma drug concentration |
| Cav | mean Serum/plasma drug concentration $\left(\text{calculated as } \frac{AUC0-\tau}{\tau}\right)$ |
| Ct | Concentration of drug at time t |
| C t(last) | Concentration of drug at time when last detectable |
| Css | Steady state serum/plasma concentration |
| DPO | Oral dose of drug |
| DIV | Intravenous dose of drug |
| F | Absolute bioavailability |
| fe% | Fraction of drug recovered in urine expressed as % of dose |
| ka | First-order absorption rate constant |
| MRT | Mean residence time |
| tlag | Lag time for absorption |
| tmax | Time of occurrence of Cmax |
| t½ | Apparent terminal half-life |

-continued

| | |
|---|---|
| Vss | Volume of distribution (steady state) |
| Vss/F | Steady state volume of distribution based on non-IV drug administration |
| Vz/F | Volume of distribution determined from terminal half-life (otherwise known as Varea, Vβ) |

The present invention relates to a novel method for improving the pharmacokinetics of tipranavir ([R-(R*,R*)]-N-[3-[1-[5,6-Dihydro-4-hydroxy-2-oxo-6-(2-phenylethyl)-6-propyl-2H-pyran-3-yl]propyl]phenyl]-5-(trifluoromethyl)-2-pyridinesulfonamide), comprising administering to a human in need of such treatment a combination of a therapeutically effective amount of tipranavir or a pharmaceutically acceptable salt thereof, and a therapeutically effective amount of ritonavir ((2S,3S,5S)-5(N-(N-((N-Methyl-N-((2-isopropyl-4-thiazoly)methyl)amino)carbonyl)-L-valinyl)amino)-2-(N-((5-thiazoly)methoxycarbonyl)amino)-1,6-diphenyl-3-hydroxhexane) or a pharmaceutically acceptable salt thereof. The structure of tipranavir is:

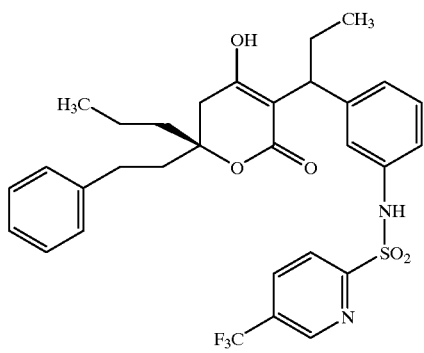

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

As is described below in Examples 1 and 2, tipranavir has been shown to lower blood levels of ritonavir. Thus, it would be expected that the level of ritonavir would be too low to have an effect on tipranavir plasma concentrations. Surprisingly, however, it has been shown that the coadministration of ritonavir and tipranavir, although resulting in a low blood level of ritonavir, results in the elevation of tipranavir plasma concentration to such an extent that a low dose of tipranavir has the same therapeutic effect as a much higher dose of tipranavir alone. This result is especially surprising when the effect of tipranavir on delavirdine is considered (see Example 3). Delavirdine, like ritonavir, inhibits cytochrome P450 monooxygenase (CYP3A), and is therefore expected to slow the clearance, and so increase blood levels, of drugs that are metabolized by CYP3A, such as tipranavir. However, although tipranavir reduces blood levels of delavirdine (just as it lowers blood levels of ritonavir), delavirdine does not effect tipranavir plasma concentrations.

When administered in combination, tipranavir and ritonavir can be formulated as separate compositions which are administered at the same time, or tipranavir and ritonavir can be administered as a single composition.

The methods of the present invention provide for the co-administration of ritonavir and tipranavir so as to inhibit retroviral proteinases and thus inhibit the replication of the virus. Thus, the methods of the invention are useful for treating patients infected with a human retrovirus, such as human immunodeficiency virus (strains of HIV-1 or HIV-2) or human T-cell leukemia viruses (HTLV-I or HTLV-II) which results in acquired immunodeficiency syndrome (AIDS) and/or related diseases. Thus, the methods of the invention are useful for inhibiting HIV protease in humans, and are also useful for inhibition, treatment, or prophylaxis of an HIV infection or AIDS in humans.

The ability of a compound to inhibit HIV protease can be demonstrated accoding to the methods disclosed in PCT application number W094/14436.

In a preferred embodiment, the invention provides a method for increasing human blood levels of tipranavir, comprising administering to a human in need of such treatment a a combination of a therapeutically effective amount of tipranavir or a pharmaceutically acceptable salt thereof, and a therapeutically effective amount of ritonavir or a pharmaceutically acceptable salt thereof.

The term human retrovirus (HRV) includes human immunodeficiency virus type I, human immunodeficiency virus type II, or strains thereof, as well as human T cell leukemia virus 1 and 2 (HTLV-1 and HTLV-2) or strains apparent to one skilled in the art, which belong to the same or related viral families and which create similar physiological effects in humans as various human retroviruses.

Patients to be treated would be those individuals: 1) infected with one or more strains of a human retrovirus as determined by the presence of either measurable viral antibody or antigen in the serum and 2) in the case of HIV, having either an asymptomatic HIV infection or a symptomatic AIDS defining infection such as i) disseminated histoplasmosis, ii) isopsoriasis, iii) bronchial and pulmonary candidiasis including pneumocystic pneumonia iv) non-Hodgkin's lymphoma or v) Kaposi's sarcoma and being less than sixty years old; or having an absolute CD4+ lymphocyte count of less than 500/mm$^3$ in the peripheral blood. Treatment would consist of maintaining an inhibitory level of the compound used according to this invention in the patient at all times and would continue until the occurrence of a second symptomatic AIDS defining infection indicates alternate therapy is needed.

More specifically, an example of one such human retrovirus is the human immunodeficiency virus (HIV, also known as HTLV-III or LAV) which has been recognized as the causative agent in human acquired immunodeficiency syndrome (AIDS), P. Duesberg, Proc. Natl. Acad. Sci. USA, 86:755 (1989). HIV contains a retro viral encoded protease, HIV-I protease, that cleaves the fusion polypeptides into the functional proteins of the mature viral particle, E. P. Lillehoj, et al., J. Virology, 62:3053 (1988); C. Debuck, et al., Proc. Natl. Acad. Sci., 84:8903 (1987). This enzyme, HIV-I protease, has been classified as an aspartyl protease and has a demonstrated homology to other aspartyl proteases such as renin, L. H. Pearl, et al., Nature 329:351 (1987); I. Katoh, et al., Nature 329:654 (1987). Inhibition of HIV-I protease blocks the replication of HIV and thus is useful in the treatment of human AIDS, E. D. Clerq, J. Med. Chem. 29:1561 (1986). Inhibitors of HIV-I protease are useful in the treatment of HIV-infected individuals who are asymptomatic or symptomatic of AIDS.

Thus, the combination tipranavir/ritonavir therapy of the present invention, which results in improved pharmacokinetics of tipranavir, is useful for treating diseases caused by retroviruses, such as human acquired immunodeficiency disease syndrome (AIDS).

Procedures by which ritonavir ((2S,3S,5S)-5(N-(N-((N-Methyl-N-((2-isopropyl-4-thiazolyl)methyl)amino)carbonyl)-L-valinyl)amino)-2-(N-((5-thiazolyl)methoxycarbonyl) amino)-1,6-diphenyl-3-hydroxhexane) may be prepared are described in PCT Patent Application No. WO94/14436, published Jul. 7, 1994, and U.S. patent application Ser. No. 08/469,965, filed Jun. 6, 1995, the contents of which are incorporated herein by reference. Procedures by which tipranavir ([R-(R*,R*)]-N-[3-[1-[5,6-Dihydro-4-hydroxy-2-oxo-6-(2-phenylethyl)-6-propyl-2H-pyran-3-yl]propyl]phenyl]-5-(trifluoromethyl)-2-pyridinesulfonamide), described in PCT Patent Application No. WO95/30670, published Nov. 16, 1995, the contents of which is incorporated by reference herein.

The tipranavir and ritonavir compounds used in the methods of the present invention may be in either free form or in protected form at one or more of the remaining (not previously protected) carboxyl, amino, hydroxy, or other reactive groups. The protecting groups may be any of those known in the art. Examples of nitrogen and oxygen protecting groups are set forth in T. W. Greene, Protecting Groups in Organic Synthesis, Wiley, N. Y., (1981); J. F. W. McOmie, ed. Protective Groups in Organic Chemistry, Plenum Press (1973); and J. Fuhrhop and G. Benzlin, Organic Synthesis, Verlag Chemie (1983). Included among the nitrogen protective groups are t-butoxycarbonyl (BOC), benzyloxycarbonyl, acetyl, allyl, phthalyl, benzyl, benzoyl, trityl and the like.

The methods of the present invention provide for the use of pharmacologically acceptable salts and/or hydrates of tipranavir and ritonavir. Pharmacologically acceptable salts refers to those salts which would be readily apparent to a manufacturing pharmaceutical chemist to be equivalent to the parent compound in properties such as formulation, stability, patient acceptance and bioavailability. Salts of ritonavir and tipranavir may include the bis-salts, such as the bis-sodium, bis-potassium and bis-calcium salts, with the bis-sodium salt being most preferred.

The methods of the present invention are useful for treating patients infected with human immunodeficiency virus (HIV) which results in acquired immunodeficiency syndrome (AIDS) and related diseases. For this indication, tipranavir and ritonavir may be administered by oral, intranasal, transdermal, subcutaneous and parenteral (including intramuscular and intravenous) routes in doses as described below.

Doses of ritonavir ranging from 100 mg to 500 mg, each administered twice daily (BID), were investigated in clinical drug-drug interaction studies of ritonavir and tipranavir. All doses of ritonavir studied were shown to have substantial and significant effects on tipranavir by elevating, or enhancing, plasma concentrations of tipranavir. Additionally, plasma tipranavir concentrations could also be altered by altering the tipranavir dose. These results indicate that a target plasma tipranavir can be achieved through various but well-defined dose combinations of ritonavir. This pharmcokinetic drug interaction is potentially of great clinical importance for a number of reasons, which include:

greater antiviral activity of tipranavir, since antiviral activity is dependent on the magnitude of plasma drug levels possibility of reducing the administered tipranavir dose, which may enhance patient compliance to antiviral therapy possibly improved safety profile since less tipranavir may be needed to elicit the desired antiviral effect.

The lowest dose of ritonavir tested, 100 mg administered twice daily, was selected on the basis that this is the only available tablet strength of ritonavir commercially available. At this dose level, ritonavir increased plasma tipranavir concentrations nearly 10-fold. The lowest median trough tipranavir concentration measured in combination with ritonavir 100 mg BID exceeded 3 $\mu$M, which is 3-fold greater than the IC90 of 1 $\mu$M reported for tipranavir.

Since the effect of ritonavir to enhance plasma tipranavir concentrations was approximately proportional to the magnitude of the ritonavir dose administered, it can be predicted that a dose of ritonavir 30 mg BID would elevate tipranavir concentrations to the target minimal therapeutic threshold of 1 $\mu$M, which is approximately 3-fold higher than the median trough of tipranavir observed in the absence of ritonavir.

In defining an upper limit for ritonavir dosing, it is important to note that a maximal, or plateau, effect for ritonavir to elevate plasma tipranavir concentrations was not achieved at the ritonavir 500 mg BID dose level, and thus higher doses of ritonavir would result in proportionately higher tipranavir concentrations. For example, at a fixed dose of tipranavir (either 600 mg BID or 900 mg BID), coadministration of ritonavir 500 mg BID resulted in an increase in trough tipranavir concentrations which was approximately 5 times greater than that observed for ritonavir 100 mg BID. Additionally, trough plasma tipranavir concentrations at a fixed ritonavir dose of 500 mg BID were proportionately dependent on the magnitude of the tipranavir dose. For example the trough tipranavir concentration for tipranavir 1350 mg BID was approximately 2-fold greater than that for tipranavir 600 mg BID, each coadministered with ritonavir 500 mg BID. Since one option for therapy may be to minimize the tipranavir dose, these results suggest that the trough plasma tipranavir concentration observed using the tipranavir 1350 mg BID/ritonavir 500 mg BID regimen is achievable using a tipranavir 600 mg BID/ritonavir 1000 mg BID regimen. It is concluded from this analysis that a low dose of tipranavir administered with a dose of ritonavir 1000 mg would result in the highest tipranavir concentrations achieved in the studies in which ritonavir and tipranavir were combined, thus supporting an upper limit for ritonavir of 1000 mg.

Similar analyses can be conducted supporting lower an upper limits for tipranavir. Based on results using the highest dose of ritonavir tested in these studies (500 mg), the lowest dose of tipranavir tested (600 mg) resulted in a trough concentration exceeding 3 $\mu$M. Since trough plasma tipranavir concentrations were dependent on the magnitude of the tipranavir dose administered, these results suggest that a tipranavir dose as low as 200 mg would successfully achieve the minimal therapeutic concentration of 1 $\mu$M. Based on the lowest dose of ritonavir tested (100 mg) and assuming a target trough tipranavir concentration equivalent to that observed for the highest dose combination tested (tipranavir 1350 mg BID/ritonavir 500 mg BID) was desired, then a tipranavir dose of 6750 mg (5×1350 mg) would be expected to be required.

Thus, these combined results of clinical studies used to investigate the pharmacokinetic drug-drug interaction involving tipranavir and ritonavir support the following limits of dosing: administration BID of a ritonavir dose of between about 30 mg to about 1000 mg, and of a tipranavir dose of between about 200 mg to about 6750 mg. Similarly, the tipranavir/ritonavir combination may be administered once a day as follows: a ritonavir dose of between about 30 mg to about 2000 mg, and of a tipranavir dose of between about 200 mg to about 13500 mg.

Those skilled in the art would know how to formulate the compounds of this invention into appropriate pharmaceutical dosage forms. Examples of the dosage forms include oral formulations, such as tablets or capsules, or parenteral formulations, such as sterile solutions.

Either solid or fluid dosage forms can be prepared for oral administration. Solid compositions are prepared by mixing the compounds of this invention with conventional ingredients such as talc, magnesium stearate, dicalcium phosphate, magnesium aluminum silicate, calcium sulfate, starch, lactose, acacia, methyl cellulose, or functionally similar pharmaceutical diluents and carriers. Capsules are prepared by mixing the compounds of this invention with an inert pharmaceutical diluent and placing the mixture into an appropriately sized hard gelatin capsule. Soft gelatin capsules are prepared by machine encapsulation of a slurry of the compounds of this invention with an acceptable inert oil such as vegetable oil or light liquid petrolatum. Syrups are prepared by dissolving the compounds of this invention in an aqueous vehicle and adding sugar, aromatic flavoring agents and preservatives. Elixirs are prepared using a hydroalcoholic vehicle such as ethanol, suitable sweeteners such as sugar or saccharin and an aromatic flavoring agent. Suspensions are prepared with an aqueous vehicle and a suspending agent such as acacia, tragacanth, or methyl cellulose.

In a preferred embodiment, the dosage form used is a self-emulsifying drug delivery system (SEDDS) microemulsion formulation. Details about SEDDS may be found in PCT Patent Applications, International Publication Nos. WO 99/06044 and WO 99/06043, both published on Feb. 11, 1999. The SEDDS formulation allows tipranavir in an exceedingly high concentration while at the same time achieving improved bioavailability. The greatly enhanced absorption afforded by this formulation appears not only to be due to its ability to solubilize tipranavir but also due to the release and dispersion of drug in submicron particles. Clinical studies have also suggested the importance of surfactants/emulsifying agents in the absorption of tipranavir.

The increase in bioavailability has the potential of effectively reducing, by a factor of one-half the number of dosing units required of the current formulation, and could have a positive impact on patient compliance. The added advantage of utilizing the free acid form of tipranavir in this formulation should also be noted.

When the compounds of this invention are administered parenterally, they can be given by injection or by intravenous infusion. Parenteral solutions are prepared by dissolving the compounds of this invention in aqueous vehicle and filter sterilizing the solution before placing in a suitable sealable vial or ampule. Parenteral suspensions are prepared in substantially the same way except a sterile suspension vehicle is used and the compounds of this invention are sterilized with ethylene oxide or suitable gas before it is suspended in the vehicle.

The exact route of administration, dose, or frequency of administration would be readily determined by those skilled in the art and is dependant on the age, weight, general physical condition, or other clinical symptoms specific to the patient to be treated.

The potential for clinically significant drug-drug interaction between tipranavir and a number of well known NRTIs, nNRTIs, and Pis is given in Table 1.

Having generally described the invention, the same will be more readily understood by reference to the following examples, which are provided by way of illustration and are not intended as limiting.

EXAMPLES

Example 1

Study 1: Pharmacokinetic Drug-Drug Interaction of Tipranavir and Ritonavir

Materials and Methods:

A multiple-dose, single treatment group was studied to assess the pharmacokinetic drug-drug interaction potential between the protease inhibitors tipranavir and ritonavir. Tipranavir was administered as a hard-filled capsule (HFC) containing 150 mg free acid equivalents of the disodium salt of tipranavir, with excipients, and ritonavir was administered as the 100-mg marketed product (Norvir). The dose was 1350 mg BID of tipranavir and 500 mg BID of ritonavir. Baseline pharmacokinetic data for each drug were obtained under steady-state conditions following 7 days of dosing. The drugs were then coadministered for 10 days, after which the pharmacokinetics of each were re-evaluated and compared with baseline data. The study was conducted in 14 healthy volunteers (13 males and 1 female) with a mean age of 29.9 years (range, 21.3–43.9 years), height of 174.4 cm (range, 162.6–185.4 cm), and weight of 76.5 kg (range, 65.1–88.2 kg). Twelve subjects were Caucasian and two were of African descent. Ten subjects completed all aspects of the study. Pharmacokinetic analyses were based on the results obtained in these subjects.

Analytical Methods:

Tipranavir in Human Plasma:

Quantitation of tipranavir in human plasma was conducted using a sensitive and selective high performance liquid chromatographic (HPLC) method. Plasma specimens (0.200 mL) were spiked with an acetonitrile solution containing the internal standard (IS), PNU-109011. The denatured proteins were separated by centrifugation and an aliquot of the supernatant was mixed with a 0.15% trifluoroacetic acid (TFA) solution in an injection vial. An aliquot (0.150 mL) was initially injected onto a short Zorbax® RX-C8 column which was connected via a column switching valve to the analytical column, Zorbax® RX-C8 column. The mobile phase was composed of acetonitrile:methanol: 0.1% TFA in water, (40:35:25, v/v). Detection was by UV absorbance at 260 nm. Retention times of tipranavir and the IS were approximately 9.9 and 13.0 minutes, respectively. Mean recoveries for tipranavir and the IS were approximately 96.6% and 95.0%, respectively.

Ritonavir in Human Plasma:

Plasma samples were assayed for ritonavir (A-84538) concentrations using a validated, sensitive and specific isocratic HPLC-UV method. Ritonavir and the internal standard (IS) were extracted from human plasma by liquid-liquid extraction with an ethyl acetate mixture. The retention times of the primary analytes were ~8.1 minutes (ritonavir), and ~12.1 minutes (IS). Mean recoveries for ritonavir and the IS were 100% and 91.4%, respectively.

Pharmacokinetic and Statistical Methods:

Pharmacokinetic parameters such as AUC, Cmax, tmax, oral clearance, and terminal half-life were determined using standard noncompartmental techniques. Treatment effects on pharmacokinetic parameters were assessed using Wilcoxon's Signed Rank Test.

Results:

Effects of Ritonavir on Tipranavir:

Mean (SD) plasma tipranavir concentrations following administration of tipranavir alone and in combination with ritonavir are shown in FIG. 1. The pharmacokinetic estimates derived from individual subject data are provided in Table 2. The median tipranavir Cmax value increased approximately 5.6-fold in the presence of ritonavir, whereas median tipranavir Cmin values increased 45-fold. On average, mean steady-state plasma tipranavir concentrations (Css) increased 12-fold following dosing with ritonavir. Of note, the increase in tipranavir concentrations was not accompanied by a prolongation of the elimination half-life (t½). This suggests the possibility that the effect of ritonavir to increase plasma tipranavir concentrations involves, in part, a pre-systemic mechanism. Speculatively, this could be due to an inhibitory effect of ritonavir on P-glycoprotein resulting in enhanced tipranavir absorption, and/or ritonavir inhibition of gut wall tipranavir metabolism.

Effects of Tipranavir on Ritonavir:

Mean (SD) plasma ritonavir concentrations following administration of ritonavir alone and in combination with tipranavir are shown in FIG. 2. The pharmacokinetic estimates derived from individual subject data are provided in Table 3. Although only 500 mg twice daily doses of ritonavir were administered in this study in healthy volunteers, the plasma ritonavir concentrations observed following dosing with ritonavir alone were slightly higher than those reported in HIV-infected patients receiving ritonavir 600 mg doses twice daily. This result supports the clinical relevance of ritonavir exposure following the doses employed in this study.

The combination of tipranavir and ritonavir dosing resulted in an approximate 5-fold decrease in mean steady-state ritonavir concentrations compared with ritonavir administered alone. The median ritonavir Cmax value decreased 3.8-fold following coadministration with tipranavir. In association with a shorter apparent half-life of elimination, the median ritonavir Cmin concentration was more than 10-fold lower when ritonavir was dosed with tipranavir compared with ritonavir dosed alone. For comparative purposes, it is interesting to note that the plasma ritonavir concentrations observed following dosing with tipranavir in this study were lower than published values for ritonavir 300 mg doses administered twice daily to HIV-infected patients. The decrease in ritonavir concentrations and shortening of the elimination half-life (t½) is consistent with metabolic induction previously attributed to tipranavir.

Discussion:

The results of this study revealed a substantial pharmacokinetic interaction involving both tipranavir and ritonavir. Ritonavir has been shown to both inhibit the metabolism of drugs which are cytochrome P450 3A (CYP3A) substrates (CYP3A is the major P450 isoform for Phase I metabolism of tipranavir), and to influence absorption through P-glycoprotein inhibition. Likewise, plasma ritonavir concentrations have been shown to be reduced by compounds (such as rifampin) known to induce metabolism.

Much less clear, however, is the prediction of quantitative effects when two drugs having these combination of properties are co-administered. The outcomes are dependent on many factors, including the doses of each administered. Given these caveats, it seems reasonable to expect that lower doses of ritonavir than employed in this study would be sufficient to substantially increase plasma tipranavir concentrations. For example, the concentrations of ABT-378, a new HIV protease inhibitor under development by Abbott Labs, are increased more than an order of magnitude following coadministration of ritonavir at doses as low as 50 mg.

Example 2

Study 2: Pharmacokinetic Drug-Drug Interaction of Tipranavir and Ritonavir

Materials and Methods:

Subject Demographics:

A multiple-dose, randomized, two treatment group was studied to further explore the pharmacokinetic drug-drug interaction potential between the protease inhibitors tipranavir and ritonavir. Tipranavir was administered as a hard-filled capsule (HFC) containing 150 mg free acid equivalents of the disodium salt of tipranavir, with excipients, and ritonavir was administered as the 100-mg marketed product (Norvir). Two fixed dose levels of tipranavir were evaluated, 600 mg BID and 900 mg BID. Both groups received their assigned dose of tipranavir continuously throughout the study period.

Within each dose group, coadministration of ritonavir was initiated at a dose of 100 mg BID after 6 days of tipranavir given alone. The dose of ritonavir was further increased in each group in a step-wise fashion to 300 mg BID and 500 mg BID after pre-defined periods of time. Baseline pharmacokinetic data were obtained for tipranavir after 6 days given alone, and then under steady-state conditions when coadministered with 100 mg or 500 mg ritonavir. Ritonavir pharmacokinetic data were obtained for the 500 mg BID dose when coadministered with tipranavir. The pharmacokinetics of tipranavir when coadministered with ritonavir were evaluated and compared with baseline data, while the ritonavir data were compared to historical data.

The study was conducted in 19 healthy volunteers (16 males and 3 females) with a mean age of 30 years (range, 19–52 years), height of 177.1 cm (range, 162.6–190.5 cm), and weight of 76.7 kg (range, 57.3–95.0 kg). Eighteen subjects were Caucasian and one was Black. Thirteen subjects completed all aspects of the study (7/600 mg tipranavir and 6/900 mg tipranavir). Pharmacokinetic analyses were based on those subjects completing the baseline evaluation and at least one period of concomitant drug administration.

Analytical Methods:

Tipranavir in Human Plasma:

Quantitation of tipranavir in human plasma was conducted using a sensitive and selective high performance liquid chromatographic (HPLC) method. Plasma specimens (0.200 mL) were spiked with an acetonitrile solution containing the internal standard (IS), PNU-109011. The denatured proteins were separated by centrifugation and an aliquot of the supernatant was mixed with a 0.15% trifluoroacetic acid (TFA) solution in an injection vial. An aliquot (0.150 mL) was initially injected onto a short Zorbax® RX-C8 column which was connected via a column switching valve to the analytical column, Zorbax® RX-C8 column. The mobile phase was composed of acetonitrile:methanol:0.1% TFA in water, (40:35:25, v/v). Detection was by UV absorbance at 260 nm. Retention times of tipranavir and the IS were approximately 11.0 and 14.5 minutes, respectively. Mean recoveries for tipranavir and the IS were approximately 96.6% and 95.0%, respectively.

Ritonavir in Human Plasma:

Plasma samples were assayed for ritonavir (A-84538) concentrations using a validated, sensitive and specific isocratic HPLC-UV method. Ritonavir and the internal standard (IS) were extracted from human plasma by liquid-liquid extraction with an ethyl acetate mixture. The retention times of the primary analytes were ~7.0 minutes (ritonavir), and ~10.0 minutes (IS). Mean recoveries for ritonavir and the IS were 101% and 91.4%, respectively.

Pharmacokinetic and Statistical Methods:

Pharmacokinetic parameters such as AUC, Cmax, tmax, oral clearance, and terminal half-life were determined using standard noncompartmental techniques.

Results:

Effects of Tipranavir on Ritonavir:

Median plasma ritonavir concentrations following administration of ritonavir 500 mg BID and either tipranavir 600 mg BID or 900 mg BID are depicted in FIG. 3. The pharmacokinetics of ritonavir derived from individual subject data are summarized in Table 4. For comparative purposes, the pharmacokinetics of ritonavir when administered alone are included in this table. The combination of ritonavir and tipranavir in this study resulted in an approximate 4-fold decrease in steady-state plasma ritonavir concentrations compared with ritonavir administered alone. Median ritonavir Cmax values were more than 2-fold lower, and Cmin values more than 10-fold lower, when ritonavir was dosed with tipranavir. The decrease in plasma ritonavir concentrations, and shortening of the elimination half-life, is consistent with metabolic induction attributable to tipranavir.

Effects of Ritonavir on Tipranavir.

Median tipranavir concentrations following tipranavir 600 mg BID administered alone and in combination with ritonavir 100 mg BID or ritonavir 500 mg BID are depicted in FIG. 4. Pharmacokinetic parameters of tipranavir derived from individual subject data are provided in Table 5. The quantitative effect of ritonavir on plasma concentrations of tipranavir was dose-related. Median AUC values of tipranavir increased approximately 9-fold following concomitant dosing of ritonavir 100 mg BID and approximately 14-fold for dosing with ritonavir 500 mg BID. Median trough tipranavir concentrations increased approximately 9-fold following dosing with ritonavir 100 mg BID, and approximately 40-fold for ritonavir 500 mg BID. Compared with tipranavir 600 mg BID administered alone, median Cmax values increased 5-fold and 7-fold, respectively, following concomitant dosing of ritonavir 100 mg and 500 mg BID, respectively. As in a previous study which assessed the pharmacokinetic drug-drug interaction of tipranavir 1350 mg BID and ritonavir 500 mg BID, no prolongation of the apparent terminal half-life of tipranavir was observed following concomitant dosing.

Median tipranavir concentrations following tipranavir 900 mg BID administered alone and in combination with ritonavir 100 mg BID and ritonavir 500 mg BID are depicted in FIG. 5. Pharmacokinetic parameters of tipranavir derived from individual subject data are provided in Table 5. As observed for the tipranavir 600 mg BID data, the quantitative effect of ritonavir on plasma concentrations of tipranavir was dose-related. Median AUC values of tipranavir increased approximately 8-fold following concomitant dosing of ritonavir 100 mg BID and approximately 20-fold for dosing with ritonavir 500 mg BID. Median trough tipranavir concentrations increased approximately 7-fold following dosing with ritonavir 100 mg BID, and approximately 45-fold for ritonavir 500 mg BID. Compared with tipranavir 900 mg BID administered alone, median Cmax values increased 5-fold and 10-fold, respectively, following concomitant dosing of ritonavir 100 mg and 500 mg BID, respectively. No prolongation of the apparent terminal half-life of tipranavir was observed following concomitant dosing.

Discussion:

A significant pharmacokinetic drug-drug interaction affecting both ritonavir and tipranavir was shown in a previous study in which tipranavir 1350 mg BID and ritonavir 500 mg BID were dosed concomitantly. The pharmacokinetic aspects of this drug interaction were further explored in this study, utilizing a combination of ritonavir and tipranavir doses. Ritonavir concentrations significantly and substantially declined following co-administration of the lowest tipranavir dose tested (600 mg BID). This finding is consistent with the results of previous studies showing that tipranavir induces its own metabolism over a wide dosage range.

Further, the effect of tipranavir to reduce plasma ritonavir concentrations was similar for doses of tipranavir ranging from 600 to 1350 mg BID, suggesting that enzyme induction of tipranavir, while substantial, appears to reach a plateau effect which occurs at or below 600 mg BID. The results of this and the previous interaction study with ritonavir support the conclusion that therapeutically relevant concentrations of ritonavir are likely not achievable following co-administration with tipranavir.

Despite the approximate 4-fold reduction in plasma ritonavir concentrations observed following concomitant tipranavir administration, ritonavir substantially and significantly increased plasma tipranavir concentrations. Importantly, a 100 mg dose of ritonavir, which is six times lower than the dose used in the treatment of HIV-infection, increased tipranavir concentrations nearly 10-fold compared with the same dose of tipranavir administered alone. As consistent with an interaction which appears to primarily result from competitive inhibition for the CYP3A receptor, tipranavir concentrations were further enhanced as the ritonavir dose increased. Likewise, at a fixed dose of ritonavir, tipranavir concentrations increased as the tipranavir dose increased. Combining the results of this study with those obtained for Protocol M/3342/0009 following ritonavir 500 mg BID dosing, for example, median trough tipranavir concentrations increased from 14.3 to 42 $\mu$M as the dose of tipranavir increased from 600 to 1350 mg BID. Thus, target tipranavir concentrations are achievable in a number of ways when tipranavir and ritonavir are co-administered, and are dependent on the magnitudes of either tipranavir or ritonavir doses.

Example 3

Pharmacokinetic Drug-Drug Interaction of Tipranavir and Delavirdine

Materials and Methods:

Subject Demographics:

The purpose of this study was to assess the effect of delavirdine administration on to the pharmacokinetics of tipranavir, and the effect of tipranavir administration on the pharmacokinetics of delavirdine. The formulation of tipranavir was bulk drug in capsule containing 300 mg free acid equivalents of the disodium salt of tipranavir, and the formulation of delavirdine was the 100-mg marketed tablet (RESCRIPTOR® Tablets). Tipranavir was administered as 1200 mg doses given BID, and delavirdine as 400 mg TID. Baseline pharmacokinetic data for each drug were obtained under pharmacokinetic steady-state conditions following 7 days of dosing. Each drug was then co-administered for 10 days, at which time the pharmacokinetics of each was re-evaluated and compared with baseline data. The study was conducted in 8 healthy volunteers (6 males and 2 females) with a mean age of 40.7 years (range, 26.3–53.9 years), height of 169 cm (range, 158–179 cm), and weight 70.2 kg (range, 59.9–82.6 kg). All subjects were Caucasian. Six subjects completed all aspects of the study. Pharmacokinetic analyses were based on results obtained in these subjects.

Analytical Methods:
Tipranavir in Human Plasma:

Quantitation of tipranavir in human plasma was conducted using a sensitive and selective high performance liquid chromatographic (HPLC) method. Plasma specimens (0.200 mL) were spiked with an acetonitrile solution containing the internal standard (IS), PNU-109011. The denatured proteins were separated by centrifugation and an aliquot of the supernatant was mixed with a 0.15% trifluoroacetic acid (TFA) solution in an injection vial. An aliquot (0.150 mL) was initially injected onto a short Zorbax® RX-C8 column which was connected via a column switching valve to the analytical column, Zorbax® RX-C8 column. The mobile phase was composed of acetonitrile:methanol:0.1% TFA in water, (40:35:25, v/v). Detection was by UV absorbance at 260 nm. Retention times of tipranavir and the IS were approximately 9.9 and 13.0 minutes, respectively. Mean recoveries for tipranavir and the IS were approximately 96.6%) and 95.0%, respectively.

Delavirdine in Human Plasma:

Plasma samples were assayed for delavirdine concentrations using a validated, sensitive and specific isocratic high performance liquid chromatographic (HPLC) method: one for the upper concentration range, and one for the lower concentration range. Delavirdine and the internal standard (IS; PNU-88822) were extracted from plasma by protein precipitation with acetonitrile. The supernatant was mixed with buffer and directly injected. Chromatographic separation was achieved using a Brownlee cyano guard column and an analytical column, DuPont Zorbax® SB CN. The mobile phase consisted of 10 mM $KH_2PO_4$ (pH 6.0): acetonitrile:methanol (20:7:7), which was run at a flow rate of 1.5 mL/min. The analytes were detected by fluorescence using an excitation wavelength of 295 nm and an emissions filter at 418 nm. The retention times of the primary analytes were ~7.5 minutes (IS) and ~8.5 minutes (delavirdine).

Pharmacokinetic and Statistical Methods:

Pharmacokinetic parameters such as AUC, Cmax, tmax, oral clearance, and terminal half-life were determined using standard noncompartmental techniques. Treatment effects on pharmacokinetic parameters were assessed using Wilcoxon's Signed Rank Test.

Results:
Effects of Delavirdine on Tipranavir:

As shown in Table 7, delavirdine had no effect on the pharmacokinetics of tipranavir.

Effects Of Tipranavir On Delavirdine:

In contrast, as shown in FIG. 6 and summarized in Table 8, co-administration of tipranavir resulted in a substantial increase in delavirdine clearance, as reflected by a marked decrease in plasma delavirdine concentrations. The median trough delavirdine concentration was more than 100-fold lower when co-administered with tipranavir, compared with delavirdine administered alone; the median delavirdine auc value was more than 20-fold lower. The magnitude of this effect on delavirdine was similar to that observed previously for coadministration of rifampin and delavirdine. These results are consistent with enzyme induction resulting from tipranavir administration and suggest the potential for other cyp3a substrates to interact with tipranavir. The lack of effect of delavirdine on tipranavir pharmacokinetics may be explained, in part, by this substantial decrease in plasma delavirdine concentrations, which are well below those expected to inhibit cyp3a.

Discussion:

Delavirdine is a non-nucleoside reverse transcriptase inhibitor, approved for use in combination with appropriate antiretroviral agents for the treatment of HIV-1 infection. Delavirdine was shown in vitro to non-competitively inhibit CYP3A. In vivo, delavirdine administered to HIV-1 infected patients at doses of 200, 300, and 400 mg TID produced rapid and significant inhibition of CYP3A, as assessed by serial erythromycin breath tests. Delavirdine has also been shown to produce a marked decrease in the clearance of other drugs that are metabolized by CYP3A, such as saquinavir and indinavir, results which are consistent with metabolic inhibition attributable to delavirdine. Conversely, drugs which induce CYP3A activity have been shown to increase the clearance of delavirdine. For example, coadministration of either rifabutin or rifampin with delavirdine produced a marked increase in delavirdine clearance and corresponding reduction in plasma delavirdine concentrations.

In vitro and in vivo data have shown that tipranavir is an enzyme inducer; the effect of coadministered tipranavir to reduce plasma delavirdine concentrations in this study further supports these findings. The reduction in plasma delavirdine concentrations was pronounced. Compared with baseline delavirdine concentrations, median trough delavirdine concentrations were more than 100-fold lower and the median delavirdine AUC value was more than 20-fold lower when delavirdine was co-administered with tipranavir. Although delavirdine has been shown in previous studies to result in significant elevations in the plasma concentrations of drugs which are metabolized by CYP3A, in this study, delavirdine had no effect on tipranavir concentrations under steady-state dosing conditions. The results of this study highlight the complexities involved in predicting the pharmacokinetic outcomes of concomitantly administering a drug which is a known enzyme inducer (for example, tipranavir) with a drug which is a known enzyme inhibitor (such as delavirdine), particularly when same isoform is involved.

It will be clear that the invention may be practiced otherwise than as particularly described in the foregoing description and examples. Numerous modifications and variations of the present invention are possible in light of the above teachings and, therefore, are within the scope of the invention. The entire disclosure of all publications cited herein are hereby incorporated by reference.

Example 4

Pharmacokinetic Drug-Drug Interaction of Tipranavir SEDDS and Ritonavir Oral Solution Materials and Methods:

Two separate multiple-dose studies with two treatment groups (tipranavir alone or tipranavir and ritonavir) were conducted to assess the pharmacokinetic drug-drug interaction potential between tipranavir and nevirapine or efavirenz. In the first 7-day period of each study, the pharmacokinetics of tipranavir were evaluated after twice-daily (BID) administration of 1250 mg tipranavir alone or with 200 mg ritonavir. Tipranvir was administered as a 250-mg SEDDS soft elastic capsule and ritonavir (Norvir) was administered as the marketed 80 mg/mL oral solution. A pharmacokinetic profile was obtained under steady-state conditions following 7 days of dosing. These studies were conducted in 48 healthy volunteers (39 males, 9 females) with a mean age of 32 years (range, 19–55 years), height of 176 cm (range, 155–193 cm), and weight of 77 kg (range, 59–95 kg). Forty-four subjects were Caucasian, 2 were Black, and 2 were Asian.

Analytical Methods:
Tipranavir in Human Plasma:

Quantitation of tipranavir in human plasma was conducted using a sensitive and selective high performance liquid chromatographic (HPLC) method. Plasma specimens (0.200 mL) were spiked with an acetonitrile solution containing the internal standard (IS), PNU-109011. The denatured proteins were separated by centrifugation and an aliquot of the supernatant was mixed with a 0.15% trifluoroacetic acid (TFA) solution in an injection vial. An aliquot (0.150 mL) was initially injected onto a short Zorbax® RX-C8 column which was connected via a column switching valve to the analytical column, Zorbax® RX-C8 column. The mobile phase was composed of acetonitrile:methanol:0.1% TFA in water, (40:35:25, v/v). Detection was by UV absorbance at 260 nm. Retention times of tipranavir and the IS were approximately 11.0 and 14.5 minutes, respectively. Mean recoveries for tipranavir and the IS were approximately 96.6% and 95.0%, respectively.

Ritonavir in Human Plasma:

Plasma samples were assayed for ritonavir (A-84538) concentrations using a validated, sensitive and specific HPLC system that was coupled with a triple quadrupole mass spectrometer for detection. Human plasma (0.200 mL) was spiked with the internal standard (IS), indinavir, buffered and added to a conditioned solid phase extraction cartridge (SPE). After elution from the SPE, a C-18AR analytical column was used to perform the chromatographic separation: the mobile phase was a gradient of methanol and 25 mM ammonium acetate. The sample was introduced by the Heated Nebulizer interface, with multiple reaction monitoring of ritonavir at 722 (molecular ion) and 296 m/z (product ion) and the IS at 614 (molecular ion) and 421 m/z (product ion), operated in the positive ion mode. Retention times were approximately 1.5 minutes. Mean recoveries for ritonavir and the IS were approximately 71.0% and 91.5%, respectively.

Pharmacokinetic and Statistical Methods.

Pharmacokinetic parameters such as AUC, Cmax, tmax, oral clearance, and terminal half-life, were determined using standard noncompartmental techniques.

Results:

Effects of Ritonavir on Tipranavir:

Mean (SD) plasma tipranavir concentrations following administration of tipranavir alone (1250 mg BID) and in combination with ritonavir (200 mg BID) are shown in FIG. 7. The pharmacokinetic estimates derived from individual subject data are provided in Table 9. Median AUC values of tipranavir were approximately 11-fold higher and median tipranavir Cmin values were about 75-fold higher in subjects receiving tipranavir with ritonavir oral solution than in subjects receiving tipranavir alone. Median Cmax values increased approximately 5-fold following concomitant dosing with ritonavir. As observed in previous studies in which tipranavir HFC and ritonavir capsules were coadministered, the apparent terminal half-life of tipranavir was not significantly affected by ritonavir.

Median (range) ritonavir pharmacokinetic parameters after administration of ritonavir oral solution 200 mg BID with tipranavir 1250 mg BID are given in Table 10. The median ritonavir AUC, Cmin, and Cmax were 12-fold, 54-fold, and 10-fold lower, respectively, for this combination compared to a 500-mg twice-daily dose of ritonavir administered alone. The apparent elimination half-life of ritonavir was also decreased relative to ritonavir given alone, which is consistent with metabolic induction by tipranavir.

Discussion:

The significant effect of ritonavir on the pharmacokinetics of tipranavir previously observed with different forms of the two drugs (tipranavir disodium salt HFC and ritonavir capsule) was also demonstrated with the combination of tipranavir SEDDS SEC and the ritonavir oral solution. The 200 mg dose of ritonavir, which is three times lower than the dose used in the treatment of HIV-1 infection, increased tipranavir steady-state concentrations by more than 10-fold compared with the same dose (1250 mg BID) of tipranavir given alone. This effect is observed despite the fact that ritonavir concentrations in the presence of tipranavir are greatly decreased.

TABLE 1

TIPRANAVIR DRUG-DRUG INTERACTION POTENTIAL

| Class | Principal Route(s) of Elimination | Potential for Clinically Significant Interaction |
|---|---|---|
| NRTIs | | |
| AZT | Conjugation/renal excretion | Low |
| 3TC | Excreted unchanged in urine | Low |
| ddI | Tubular secretion ~55% in urine; other? | Low |
| ddC | Excreted unchanged in urine | Low |
| d4T | Tubular secretion ~40% in urine; other? | Low |
| Abacavir | Glucuronidation and carboxylation | Low |
| nNRTIs | | |
| Delavirdine | CYP3A, CYP2D6 | High (and unfavorable) |
| | | (Tipranavir decreased delavirdine AUC > 95%) |
| PNU-142721 | Conjugation, CYP3A | Uncertain |
| Efavirenz | CYP3A | Uncertain |
| (DMP-266) | | (Efavirenz is a possible CYP3A inducer) |
| Protease Inhibitors | | |
| Effect of Tipranavir on another PI | | |
| Nevirapine | CYP2B6, CYP3A | Uncertain |
| | | (Rifampin decreases nevirapine concentrations ~40%) |
| Indinavir | CYP3A (also CYP2C9 for nelfinavir) | High (and unfavorable) |
| Nelfinavir | | (Rifampin decreased AUC by ~80%) |
| Amprenavir | | |
| Saquinavir | | |

TABLE 1-continued

TIPRANAVIR DRUG-DRUG INTERACTION POTENTIAL

| Class | Principal Route(s) of Elimination | Potential for Clinically Significant Interaction |
|---|---|---|
| Effect of another PI on Tipranavir | | |
| Ritonavir | CYP3A, CYP2D6 | High (possibly favorable) (Ritonavir increases trough tipranavir concentrations; tipranavir expected to reduce ritonavir concentrations) |

TABLE 2

Median (Range) Tipranavir Pharmacokinetic Parameters after Tipranavir 1350 mg BID (n = 10)

| Parameter | Tipranavir Alone | Tipranavir + Ritonavir 500 mg BID | Statistics* |
|---|---|---|---|
| CLPO (L/h) | 31 (11–100) | 1.9 (1.2–3.8) | p < .05 |
| AUCτ ($\mu$M-h) | 74 (23–202) | 1202 (586–1935) | p < .05 |
| Css ($\mu$M) | 6.1 (1.9–16.8) | 100 (49–161) | p < .05 |
| Cmin ($\mu$M) | 0.78 (0.34–1.42) | 42 (12–84) | p < .05 |
| Cmax ($\mu$M) | 26 (8.2–57.5) | 189 (93–278) | p < .05 |
| Tmax (h) | 2.0 (1.0–3.0) | 3.0 (2.0–5.0) | p < .05 |
| t½ (h)† | —‡ | 3.9 (3.3–5.1) | nc |

*nc = not calculated
†Harmonic mean
‡Could not be calculated with acceptable accuracy

TABLE 3

Median (Range) Ritonavir Pharmacokinetic Parameters after Ritonavir 500 mg BID (n = 10)

| Parameter | Ritonavir Alone | Ritonavir + Tipranavir 1350 mg BID | Statistics* |
|---|---|---|---|
| CLPO (L/h) | 5.1 (3.9–7.8) | 26 (17–61) | p < .05 |
| AUCτ ($\mu$g · h/mL) | 100 (64–128) | 19 (8.2–30.0) | p < .05 |
| Css ($\mu$g/mL) | 8.4 (5.3–10.7) | 1.6 (0.69–2.50) | p < .05 |
| Cmin ($\mu$g/mL) | 1.9 (1.0–3.9) | 0.10 (0.04–0.29) | p < .05 |
| Cmax ($\mu$g/mL) | 19 (12–28) | 4.8 (2.2–10.1) | p < .05 |
| Tmax (h) | 3.0 (1.0–4.0) | 3.0 (2.0–4.0) | NS |
| t½ (h)† | 2.9 (2.6–4.4) | 1.8 (1.3–2.1) | nc |

*NS = not significant (p > .05); nc = not calculated
†Harmonic mean

TABLE 4

Median (Range) Ritonavir Pharmacokinetic Parameters after Ritonavir 500 mg BID Co-administered with Tipranavir

| Parameter | Ritonavir Alone* | Ritonavir + Tipranavir 600 mg BID† | Ritonavir + Tipranavir 900 mg BID‡ |
|---|---|---|---|
| CLPO (L/h) | 5.1 (3.9–7.8) | 19 (11–31) | 19 (12–27) |
| AUCτ ($\mu$g · h/mL) | 100 (64–128) | 27 (16–44) | 26 (19–40) |
| Css ($\mu$g/mL) | 8.4 (5.3–10.7) | 2.3 (1.4–3.7) | 1.9 (1.6–3.4) |
| Cmin ($\mu$g/mL) | 1.9 (1.0–3.9) | 0.15 (0.08–0.53) | 0.15 (0.09–0.62) |
| Cmax ($\mu$g/mL) | 19 (12–28) | 7.0 (4.8–8.5) | 5.8 (3.9–7.9) |
| Tmax (h) | 3.0 (1.0–4.0) | 3.0 (2.0–4.0) | 3.0 (2.0–4.0) |
| t½ (h)§ | 2.9 (2.6–4.4) | 1.8 (1.5–2.2) | 1.8 (1.5–2.7) |

*Taken from the results of Protocol M/3342/0009
†N = 7
‡N = 6
§Harmonic mean

TABLE 5

Median (Range) Tipranavir Pharmacokinetic Parameters (n = 7) after Tipranavir 600 mg BID Given Alone or Co-administered with Ritonavir

| Parameter | Tipranavir Alone | Tipranavir + RTV 100 mg BID | Tipranavir + RTV 500 mg BID |
|---|---|---|---|
| CLPO (L/h) | 31.3 (17.3–88.8) | 3.35 (2.44–6.07) | 2.23 (1.02–4.79) |
| AUCτ ($\mu$M · h) | 32.5 (11.3–57.5) | 297 (164–407) | 446 (207–972) |
| Css ($\mu$M) | 2.70 (0.94–4.79) | 24.8 (13.7–34.0) | 37.2 (17.3–81.0) |
| Cmin ($\mu$M) | 0.341 (0.165–0.929) | 3.14 (1.61–12.8) | 14.3 (4.70–32.5) |
| Cmax ($\mu$M) | 11.3 (4.18–19.1) | 56.8 (32.5–75.4) | 78.6 (36.6–144.0) |
| tmax (h) | 2.0 (1.0–4.0) | 2.0 (1.5–3.0) | 2.0 (2.0–3.0) |
| t½ (h)* | 3.6 (2.9–4.8) | 2.3 (1.8–4.1) | 3.7 (2.8–4.8) |

*Harmonic mean

TABLE 6

Median (Range) Tipranavir Pharmacokinetic Parameters (n = 6) after Tipranavir 900 mg BID Given Alone or Co-administered with Ritonavir

| Parameter | Tipranavir Alone | Tipranavir + RTV 100 mg BID | Tipranavir + RTV 500 mg BID |
|---|---|---|---|
| CLPO (L/h) | 32.4 (20.8–53.1) | 4.10 (2.45–7.86) | 1.64 (1.00–2.82) |
| AUCτ ($\mu$M · h) | 46.5 (28.1–71.8) | 368 (190–610) | 913 (530–1,497) |
| Css ($\mu$M) | 3.88 (2.34–5.98) | 30.6 (15.8–50.8) | 76.1 (44.1–124.8) |
| Cmin ($\mu$M) | 0.499 (0.160–1.150) | 3.62 (1.98–6.95) | 22.7 (9.91–63.2) |
| Cmax ($\mu$M) | 14.6 (9.38–24.8) | 68.9 (39.7–129.0) | 148 (122–187) |
| tmax (h) | 2.0 (1.5–3.0) | 3.0 (2.0–4.0) | 2.0 (2.0–3.0) |
| t½ (h)* | 4.2 (2.6–6.8) | 1.9 (1.6–2.4) | 3.5 (3.0–5.3) |

*Harmonic mean

TABLE 7

Median (Range) Tipranavir Pharmacokinetic Parameters after Tipranavir 1200 mg BID

| Parameter | Tipranavir Alone | Tipranavir + DLV 400 mg TID | Statistics |
|---|---|---|---|
| CLPO (L/h) | 28.1 (11–70) | 25.6 (13–64) | NS* |
| AUCτ (μM · h) | 80.9 (29–182) | 80.0 (31–153) | NS |
| Css (μM) | 6.74 (2.4–15) | 6.67 (2.6–13) | NS |
| Cmin (μM) | 0.64 (0.20–1.3) | 0.85 (0.13–1.4) | NS |
| Cmax (μM) | 25.1 (5.0–46) | 23.0 (8.3–47) | NS |
| tmax (h) | 1.8 (1.0–4.0) | 2.5 (2.0–3.0) | NS |
| t½ (h)* | 3.4 (1.6–4.6) | 2.4 (1.5–3.6) | NS |

*NS = Not significant (p > .05).

TABLE 8

Median (Range) Delavirdine Pharmacokinetic Parameters after Delavirdine Mesylate 400 mg TID

| Parameter | Delavirdine Alone | Delavirdine + Tipranavir 1200 mg BID | Statistics |
|---|---|---|---|
| CLPO (L/h) | 5.18 (1.5–7.8) | 118 (60–465) | p > .05 |
| AUCτ (μM · h) | 171 (93–491) | 6.3 (1.6–12.0) | p > .05 |
| Css (μM) | 21.4 (12–61) | 0.79 (0.19–1.5) | p > .05 |
| Cmin (μM) | 12.7 (4.2–41) | 0.09 (0.0–0.14) | p > .05 |
| Cmax (μM) | 31.1 (17–81) | 2.16 (0.53–3.9) | p > .05 |
| Tmax (h) | 1.2 (1.0–2.0) | 1.8 (1.0–3.0) | NS |
| t½ (h)* | 4.7 (3.0–6.3) | 1.3 (1.2–2.1) | p > .05 |
| CLf/CLm | 0.16 (0.09–0.23) | 1.9 (1.5–2.6) | p > .05 |

*NS = Not significant (p > .05).

TABLE 9

Median (Range) Tipranavir Pharmacokinetic Parameters after Tipranavir SEDDS SEC 1250 mg BID Given Alone Or Coadministered with Ritonavir Oral Solution 200 mg BID

| Parameter | TPV (N = 22) | TPV + RTV (N = 21) |
|---|---|---|
| CLPO (L/h) | 12.7 (6.1–23.7) | 1.19 (0.47–2.29) |
| AUCτ (μM · h) | 163 (88–338) | 1745 (906–4448) |
| Css (μM) | 13.6 (7.3–28.1) | 145 (76–371) |
| Cmin (μM) | 0.82 (0.30–2.20) | 62.1 (11.2–261) |
| Cmax (μM) | 56.0 (23.5–99.4) | 271 (148–434) |
| tmax (h) | 2.0 (2.0–4.0) | 3.0 (1.5–4.0) |
| t½ (h)* | 5.4 (1.8–12.1) | 3.8 (2.7–12.5) |

TABLE 10

Median (Range) Ritonavir Pharmacokinetic Parameters after Ritonavir Oral Solution 200 mg BID Coadministered with Tipranavir SEDDS SEC 1250 mg BID

| Parameter | RTV (N = 22) |
|---|---|
| CLPO (L/h) | 25.1 (8.4–73.1)* |
| AUCτ (μg · h/mL) | 8.0 (2.7–23.9)* |
| Css (μg/mL) | 0.67 (0.23–1.99)* |
| Cmin (μg/mL) | 0.035 (0.000–0.341)* |
| Cmax (μg/mL) | 2.0 (0.7–4.4) |
| tmax (h) | 3.0 (0.5–4.0) |
| t½ (h)* | 1.7 (1.3–2.9) |

*N = 21

We claim:

1. A method for improving the pharmacokinetics of tipranavir, comprising administering to a human in need of such treatment a combination of a therapeutically effective amount of tipranavir or a pharmaceutically acceptable salt thereof, and a therapeutically effective amount of ritonavir or a pharmaceutically acceptable salt thereof.

2. The method of claim 1, wherein said therapeutically effective amount of tipranavir is between about 200 mg and about 6750 mg of tipranavir, and said therapeutically effective amount of ritonavir is between about 30 mg and about 1000 mg of ritonavir.

3. The method of claim 1, wherein said therapeutically effective amount of tipranavir is between about 200 and about 900 mg of tipranavir, and said therapeutically effective amount of ritonavir is between about 30 and about 500 mg of ritonavir.

4. The method of claim 1, wherein said therapeutically effective amount of tipranavir is between about 200 and about 900 mg of tipranavir, and said therapeutically effective amount of ritonavir is between about 30 and about 300 mg of ritonavir.

5. The method of claim 1, wherein said therapeutically effective amount of tipranavir is between about 200 and about 600 mg of tipranavir, and said therapeutically effective amount of ritonavir is between about 30 and about 500 mg of ritonavir.

6. The method of claim 1, wherein said therapeutically effective amount of tipranavir is between about 200 and about 600 mg of tipranavir, and said therapeutically effective amount of ritonavir is between about 30 and about 300 mg of ritonavir.

7. The method of claim 1, wherein said therapeutically effective amount of tipranavir is between about 200 and about 600 mg of tipranavir, and said therapeutically effective amount of ritonavir is between about 30 and about 100 mg of ritonavir.

8. A method for increasing human blood levels of tipranavir, comprising administering to a human in need of such treatment a combination of a therapeutically effective amount of tipranavir or a pharmaceutically acceptable salt thereof, and a therapeutically effective amount of ritonavir or a pharmaceutically acceptable salt thereof.

9. The method of claim 8, wherein said therapeutically effective amount of tipranavir is between about 200 mg and about 6750 mg of tipranavir, and said therapeutically effective amount of ritonavir is between about 30 mg and about 1000 mg of ritonavir.

10. The method of claim 8, wherein said therapeutically effective amount of tipranavir is between about 200 and about 900 mg of tipranavir, and said therapeutically effective amount of ritonavir is between about 30 and about 500 mg of ritonavir.

11. The method of claim 8, wherein said therapeutically effective amount of tipranavir is between about 200 and about 900 mg of tipranavir, and said therapeutically effective amount of ritonavir is between about 30 and about 300 mg of ritonavir.

12. The method of claim 8, wherein said therapeutically effective amount of tipranavir is between about 200 and about 600 mg of tipranavir, and said therapeutically effective amount of ritonavir is between about 30 and about 500 mg of ritonavir.

13. The method of claim 8, wherein said therapeutically effective amount of tipranavir is between about 200 and about 600 mg of tipranavir, and said therapeutically effective amount of ritonavir is between about 30 and about 300 mg of ritonavir.

14. The method of claim 8, wherein said therapeutically effective amount of tipranavir is between about 200 and about 600 mg of tipranavir, and said therapeutically effective amount of ritonavir is between about 30 and about 100 mg of ritonavir.

* * * * *